United States Patent
Hissong et al.

(10) Patent No.: US 6,413,254 B1
(45) Date of Patent: Jul. 2, 2002

(54) METHOD OF TONGUE REDUCTION BY THERMAL ABLATION USING HIGH INTENSITY FOCUSED ULTRASOUND

(75) Inventors: James B. Hissong; Fred B. Dinger, both of Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/487,707

(22) Filed: Jan. 19, 2000

(51) Int. Cl.[7] ................................................ A61N 1/18
(52) U.S. Cl. ........................ 606/27; 606/31; 601/2; 601/3; 607/96; 607/134; 128/898
(58) Field of Search ............................... 604/22; 606/41, 606/45, 46, 49, 169, 170, 171, 27–31; 607/101, 105, 134, 135, 96; 601/2, 3; 128/898

(56) References Cited

U.S. PATENT DOCUMENTS

| | | |
|---|---|---|
| 3,990,452 A | 11/1976 | Murry et al. |
| 4,658,828 A | 4/1987 | Dory |
| 4,807,633 A | 2/1989 | Fry |
| 4,858,613 A | 8/1989 | Fry et al. |
| 4,917,096 A | 4/1990 | Engelhart et al. |
| 4,951,653 A | 8/1990 | Fry et al. |
| 4,955,365 A | 9/1990 | Fry et al. |
| RE33,590 E | 5/1991 | Dory |
| 5,033,456 A | 7/1991 | Pell et al. |
| 5,036,855 A | 8/1991 | Fry et al. |
| 5,054,470 A | 10/1991 | Fry et al. |
| 5,065,761 A | 11/1991 | Pell |
| 5,080,101 A | 1/1992 | Dory |
| 5,080,102 A | 1/1992 | Dory |
| 5,117,832 A | 6/1992 | Sanghvi et al. |
| 5,134,988 A | 8/1992 | Pell et al. |
| 5,143,074 A | 9/1992 | Dory |
| 5,150,711 A | 9/1992 | Dory |
| 5,150,712 A | 9/1992 | Dory |
| 5,158,070 A | 10/1992 | Dory |
| 5,222,501 A | 6/1993 | Ideker et al. |
| 5,247,935 A | 9/1993 | Cline et al. |
| 5,267,954 A | 12/1993 | Nita |
| 5,269,291 A | 12/1993 | Carter |
| 5,269,297 A | 12/1993 | Weng et al. |
| 5,295,484 A | 3/1994 | Marcus et al. |

(List continued on next page.)

FOREIGN PATENT DOCUMENTS

WO     WO97/43970     11/1997

OTHER PUBLICATIONS

Nov. 5, 1998 Company Press Release—FDA Clears First-of-its-Kind Device for Treatment of Sleep Disorder Affecting 20 Million Americans, 4pgs.

(List continued on next page.)

*Primary Examiner*—John P. Leubecker
*Assistant Examiner*—David M. Ruddy

(57) ABSTRACT

A method of tongue reduction by thermal ablation using high intensity focused ultrasound includes the steps of introducing an ultrasound emitting member in a patient's oral cavity, positioning the ultrasound emitting member adjacent an external surface of the tongue, emitting ultrasound energy from the ultrasound emitting member into tissue of the tongue, focusing the ultrasound energy within the tongue at a focusing zone contained in a target area disposed beneath the external surface, heating the tissue with the focused ultrasound energy such that the tissue at the target area is heated to an ablative temperature to form a lesion and withdrawing the ultrasound emitting member from the oral cavity. The lesion is allowed to be absorbed by the patient's body and/or to remain as altered tissue such that the tongue is reduced in size to correspondingly increase the size of the patient's airway and/or is stiffened to resist vibration. The lesion begins a predetermined distance from the external surface of the tongue such that the mucosa remains undamaged and preserved.

39 Claims, 5 Drawing Sheets

U.S. PATENT DOCUMENTS

| | | | |
|---|---|---|---|
| 5,304,115 | A | 4/1994 | Pflueger et al. |
| 5,312,328 | A | 5/1994 | Nita et al. |
| 5,318,014 | A | 6/1994 | Carter |
| 5,342,292 | A | 8/1994 | Nita et al. |
| 5,354,258 | A | 10/1994 | Dory |
| 5,380,274 | A | 1/1995 | Nita |
| 5,391,197 | A | 2/1995 | Burdette |
| 5,397,301 | A | 3/1995 | Pflueger et al. |
| 5,409,002 | A | 4/1995 | Pell |
| 5,417,672 | A | 5/1995 | Nita et al. |
| 5,423,812 | A | 6/1995 | Ellman et al. |
| 5,431,621 | A | 7/1995 | Dory |
| 5,431,663 | A | 7/1995 | Carter |
| 5,447,509 | A | 9/1995 | Miller et al. |
| 5,456,662 | A | 10/1995 | Edwards |
| 5,474,530 | A | 12/1995 | Passafaro et al. |
| 5,492,126 | A | 2/1996 | Hennige et al. |
| 5,501,655 | A | 3/1996 | Rolt et al. |
| 5,514,131 | A | 5/1996 | Edwards |
| 5,520,188 | A | 5/1996 | Hennige et al. |
| 5,542,917 | A | 8/1996 | Nita et al. |
| 5,620,479 | A | 4/1997 | Diederich |
| 5,624,439 | A | 4/1997 | Edwards |
| 5,674,191 | A | 10/1997 | Edwards |
| 5,676,692 | A | 10/1997 | Sanghvi et al. |
| 5,707,349 | A | 1/1998 | Edwards |
| 5,718,702 | A | 2/1998 | Edwards |
| 5,728,094 | A | 3/1998 | Edwards |
| 5,730,719 | A | 3/1998 | Edwards |
| 5,733,315 | A | 3/1998 | Burdette et al. |
| 5,735,280 | A | 4/1998 | Sherman et al. |
| 5,738,114 | A | 4/1998 | Edwards |
| 5,743,870 | A | 4/1998 | Edwards |
| 5,743,904 | A | 4/1998 | Edwards |
| 5,746,224 | A * | 5/1998 | Edwards et al. ............... 606/41 |
| 5,762,066 | A | 6/1998 | Law et al. |
| 5,800,379 | A | 9/1998 | Edwards |
| 5,800,429 | A | 9/1998 | Edwards |
| 5,800,482 | A | 9/1998 | Pomeranz et al. |
| 5,807,308 | A | 9/1998 | Edwards |
| 5,817,049 | A | 10/1998 | Edwards |
| 5,823,197 | A | 10/1998 | Edwards |
| 5,827,277 | A | 10/1998 | Edwards |
| 5,843,077 | A | 12/1998 | Edwards |
| 5,871,524 | A | 2/1999 | Knowlton |
| 5,873,845 | A | 2/1999 | Cline et al. |
| 5,873,902 | A | 2/1999 | Sanghvi et al. |
| 5,879,349 | A | 3/1999 | Edwards |
| 5,882,302 | A | 3/1999 | Driscoll, Jr. et al. |
| 5,895,356 | A * | 4/1999 | Andrus et al. ................. 601/3 |
| 5,928,169 | A | 7/1999 | Schätzle et al. |
| 5,938,608 | A | 8/1999 | Bieger et al. |
| 5,984,881 | A | 11/1999 | Ishibashi et al. |
| 5,984,882 | A | 11/1999 | Rosenschein et al. |
| 6,007,499 | A | 12/1999 | Martin et al. |
| 6,026,816 | A * | 2/2000 | McMillan et al. .......... 128/898 |
| 6,096,033 | A | 8/2000 | Tu et al. |
| 6,113,559 | A * | 9/2000 | Klopotek et al. ............... 601/3 |
| 6,126,657 | A * | 10/2000 | Edwards et al. .............. 606/45 |
| 6,135,971 | A | 10/2000 | Hutchinson et al. |
| 6,210,355 | B1 * | 4/2001 | Edwards et al. ............ 607/134 |
| 6,217,530 | B1 * | 4/2001 | Martin et al. .................. 601/2 |
| 6,241,753 | B1 * | 6/2001 | Knowlton ................... 607/101 |
| 6,309,355 | B1 * | 10/2001 | Cain et al. ..................... 601/2 |
| 6,325,769 | B1 * | 12/2001 | Klopotek ....................... 601/2 |

OTHER PUBLICATIONS

May 5, 1998 Clinical Investigations—Radiofrequency Volumetric Tissue Reduction of the Palate in Subjects with Sleep–Disordered Breathing, Nelson B. Powell, MD; Robert W. Riley; Robert J. Troell, MD; Kasey Li, MD; Marc B. Blumen, MD; Christian Guilleminault, MD, 12 pages.

Jan. 6 1999 Somnoplasty for Obstructive Sleep Apnea, 1 page.

Jan. 6, 1999 Somnoplasty For the Treatment of Snoring, 2 pgs.

Feb. 17, 1999 Sonablate Technology with HIFU, 2 pages.

Feb. 23, 1999 Focus Surgery, (McDonald & Company), 1 page.

May 5, 1997 Laboratory and animal investigations—Radiofrequency Volumetric Reduction of the Tongue, Nelson B. Powell, MD; Robert W. Riley, MD; Robert J. Troell, MD; Marc B. Blumen, MD; Christian Guilleminault, MD, 8 pages.

* cited by examiner

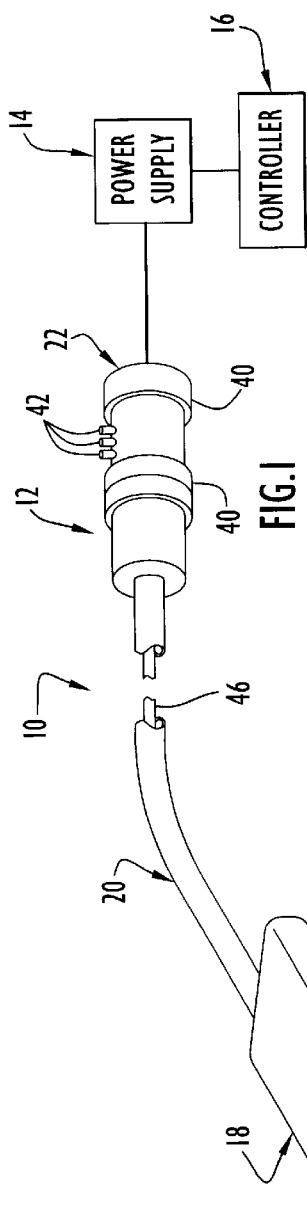
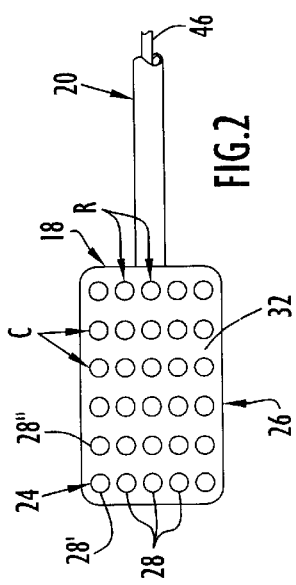
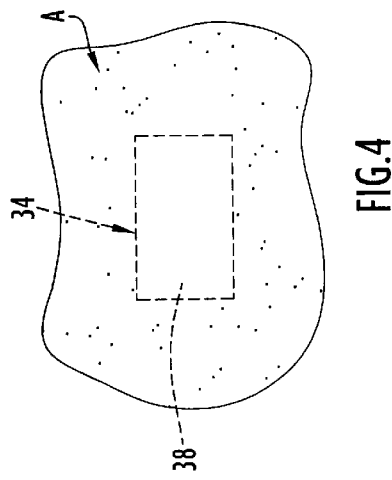
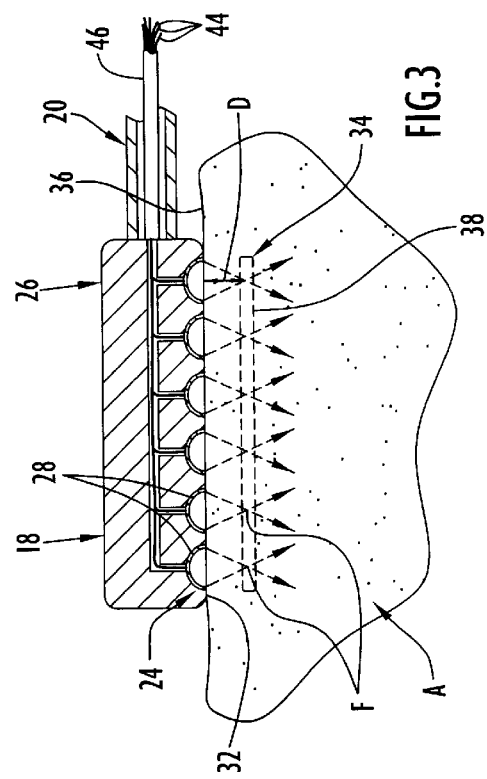

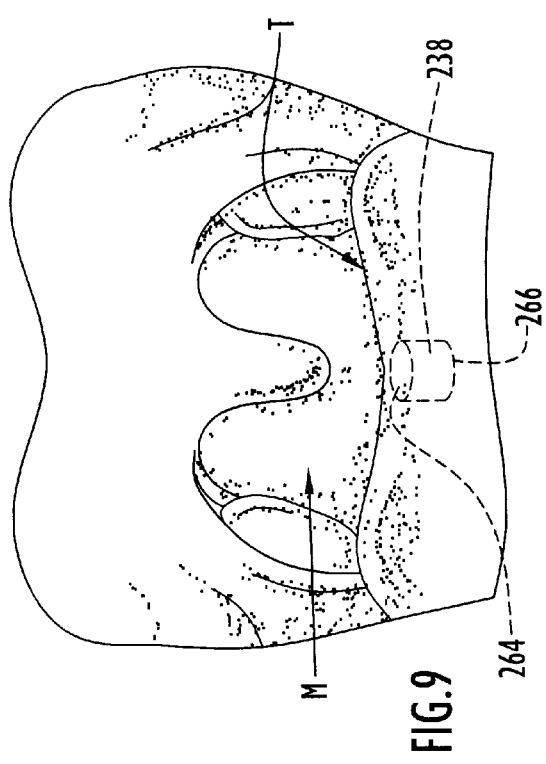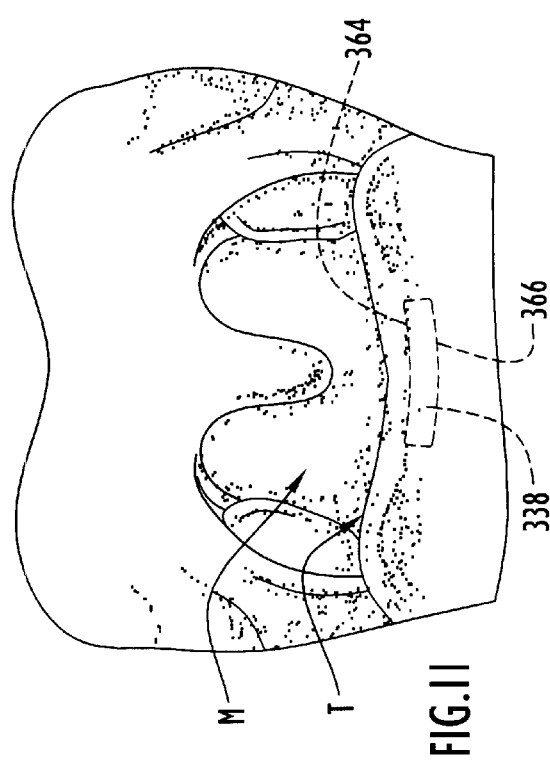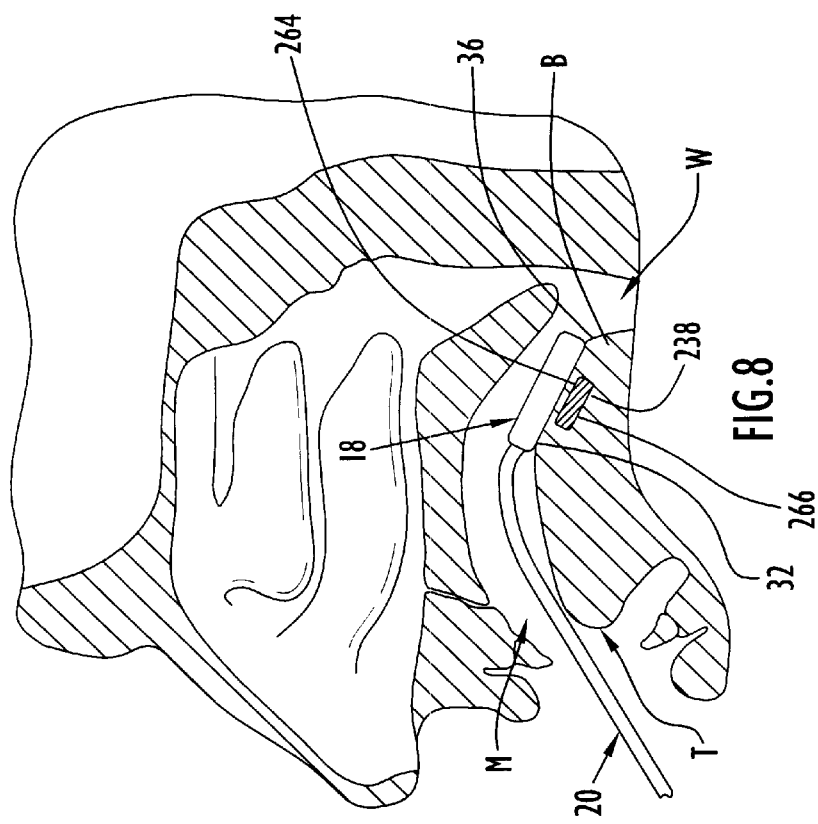

METHOD OF TONGUE REDUCTION BY THERMAL ABLATION USING HIGH INTENSITY FOCUSED ULTRASOUND

CROSS-REFERENCE TO RELATED PATENT APPLICATIONS

This application is related to co-pending U.S. patent applications entitled Methods of Soft Palate Reduction By Thermal Ablation Using High Intensity Focused Ultrasound, Methods of Tonsil Reduction By Thermal Ablation Using High Intensity Focused Ultrasound, Methods of Turbinate Or Other Soft Tissue Reduction By Thermal Ablation Using High Intensity Focused Ultrasound, Methods of Skin Rejuvenation By Thermal Stimulation Using High Intensity Focused Ultrasound, Focused Ultrasound Ablation Devices Having Malleable Handle Shafts and Methods of Using the Same, and Focused Ultrasound Ablation Devices Having Selectively Actuatable Ultrasound Emitting Elements and Methods of Using the Same, the disclosures of which are incorporated herein by reference.

BACKGROUND OF THE INVENTION

1. Field of the Invention

The present invention relates generally to the treatment of anatomical tissue of the head and/or neck with high intensity focused ultrasound energy and, more particularly, to reduction of the tongue by thermal ablation using high intensity focused ultrasound.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at one or more specific focusing zones within the tissue, thermal effects can be confined to a defined location, region, volume or area, and such location, region, volume or area can be remote from the ultrasound emitting member.

With the use of high intensity focused ultrasound (HIFU) one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue at the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue at a target location, volume, region or area to an ablative temperature creates an ablative lesion in the tissue at the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue at a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various devices and/or methods for treating anatomical tissue with ultrasound have been proposed as represented by U.S. Pat. No. Re. 33,590 to Dory, U.S. Pat. No. 3,990,452 to Murry et al, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,033,456 to Pell et al, U.S. Pat. No. 5,036,855 to Fry et al, U.S. Pat. No. 5,054,470 to Fry et al, U.S. Pat. No. 5,065,761 to Pell, U.S. Pat. No. 5,080,101 to Dory, U.S. Pat. No. 5,080,102 to Dory, U.S. Pat. No. 5,117,832 to Sanghvi et al, U.S. Pat. No. 5,134,988 to Pell et al, U.S. Pat. No. 5,143,074 to Dory, U.S. Pat. No. 5,150,711 to Dory, U.S. Pat. No. 5,150,712 to Dory, U.S. Pat. No. 5,158,070 to Dory, U.S. Pat. No. 5,222,501 to Ideker et al, U.S. Pat. No. 5,267,954 to Nita, U.S. Pat. No. 5,269,291 to Carter, U.S. Pat. No. 5,269,297 to Weng et al, U.S. Pat. No. 5,295,484 to Marcus et al, U.S. Pat. No. 5,304,115 to Pflueger et al, U.S. Pat. No. 5,312,328 to Nita et al, U.S. Pat. No. 5,318,014 to Carter, U.S. Pat. No. 5,342,292 to Nita et al, U.S. Pat. No. 5,354,258 to Dory, U.S. Pat. No. 5,380,274 to Nita, U.S. Pat. No. 5,391,197 to Burdette et al, U.S. Pat. No. 5,397,301 to Pflueger et al, U.S. Pat. No. 5,409,002 to Pell, U.S. Pat. No. 5,417,672 to Nita et al, U.S. Pat. No. 5,431,621 to Dory, U.S. Pat. No. 5,431,663 to Carter, U.S. Pat. No. 5,447,509 to Mills et al, U.S. Pat. No. 5,474,530 to Passafaro et al, U.S. Pat. No. 5,492,126 to Hennige et al, U.S. Pat. No. 5,501,655 to Rolt et al, U.S. Pat. No. 5,520,188 to Hennige et al, U.S. Pat. No. 5,542,917 to Nita et al, U.S. Pat. No. 5,620,479 to Diederich, U.S. Pat. No. 5,676,692 to Sanghvi et al, U.S. Pat. No. 5,728,094 to Edwards, U.S. Pat. No. 5,730,719 to Edwards, U.S. Pat. No. 5,733,315 to Burdette et al, U.S. Pat. No. 5,735,280 to Sherman et al, U.S. Pat. No. 5,738,114 to Edwards, U.S. Pat. No. 5,746,224 to Edwards, U.S. Pat. No. 5,762,066 to Law et al, U.S. Pat. No. 5,800,379 to Edwards, U.S. Pat. No. 5,800,429 to Edwards, U.S. Pat. No. 5,800,482 to Pomeranz et al, U.S. Pat. No. 5,807,308 to Edwards, U.S. Pat. No. 5,817,049 to Edwards, U.S. Pat. No. 5,823,197 to Edwards, U.S. Pat. No. 5,827,277 to Edwards, U.S. Pat. No. 5,843,077 to Edwards, U.S. Pat. No. 5,871,524 to Knowlton, U.S. Pat. No. 5,873,845 to Cline et al, U.S. Pat. No. 5,873,902 to Sanghvi et al, U.S. Pat. No. 5,879,349 to Edwards, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al.

In particular, the use of high intensity focused ultrasound to thermally damage, ablate, coagulate, denature, cauterize, necrotize or destroy a target volume of tissue is exemplified by U.S. Pat. No. Re. 33,590 to Dory, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,036,855 to Fry et al, U.S. Pat. No. 5,054,470 to Fry et al, U.S. Pat. No. 5,080,101 to Dory, U.S. Pat. No. 5,080,102 to Dory, U.S. Pat. No. 5,117,832 to Sanghvi et al, U.S. Pat. No. 5,143,074 to Dory, U.S. Pat. No. 5,150,711 to Dory, U.S. Pat. No. 5,150,712 to Dory, U.S. Pat. No. 5,295,484 to Marcus et al, U.S. Pat. No. 5,354,258 to Dory, U.S. Pat. No. 5,391,197 to Burdefte et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,733,315 to Burdette et al, U.S. Pat. No. 5,762,066 to Law et al, U.S. Pat. No. 5,871,524 to Knowlton, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al.

Ablation of anatomical tissue of the head and/or neck in order to treat various airway related disorders or conditions, such as airway obstructions, snoring disorders and sleep apnea syndrome, has been proposed as illustrated by U.S. Pat. No. 5,423,812 to Ellman et al, U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077 and 5,879,349 to Edwards and WO 97/43970. The latter patents disclose ablation of various structures of the anatomical airway to alleviate or eliminate snoring disorders and/or obstructive sleep apnea syndrome in patients. U.S. Pat. No. 5,423,812 relates to electrosurgical stripping of tissue. U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077, 5,879,349 and WO97/43970 disclose RF ablation using tissue penetrating electrodes. U.S. Pat. Nos. 5,707,349, 5,728,094, 5,730,719, 5,738,114, 5,746,224, 5,800,379, 5,800,429, 5,807,308, 5,817,049, 5,823,197, 5,827,277, 5,843,077 and 5,879,349 refer to ultrasound as a possible source of ablative energy.

Depending on the thickness, size and/or shape of the tongue in relation to other tissues or anatomical structures of the airway, the tongue may present an airway restriction or obstruction and/or source of resonance or vibration causing or contributing to snoring disorders and/or obstructive sleep apnea syndrome. For example, one type of snoring disorder results from obstruction of the oropharyngeal isthmus by other tissue or structures of the airway. When the oropharyngeal isthmus or another portion of the airway is/are obstructed or restricted, such as by the tongue or other tissues and/or anatomical structures of the airway, an interruption in or cessation of breathing may occur resulting in obstructive sleep apnea syndrome. Sleep apnea syndrome is a medical condition characterized by episodes of apnea during sleep causing daytime hypersomnomulence, morning arm aches, intellectual deterioration, cardiac arrythmias, snoring and/or thrashing during sleep.

Treatments for snoring disorders and/or sleep apnea syndrome have included various pharmacological, surgical and physical measures to reduce or eliminate tissue vibrations and/or airway obstructions or restrictions so as to enhance the flow of air through the patient's airway. Pharmacological measures have included the use of medications such as protriptyline, medroxyprogesterone, acetazolamide, theophylline, nicotine and other medications in addition to avoidance of central nervous system depressants such as sedatives or alcohol. Such medications typically have undesirable side effects and are of limited effectiveness. Surgical measures have included uvulopalatal pharyngoplasty, tonsillectomy, surgery to correct severe retrognathia and tracheostomy. Another surgical measure has involved pulling the tongue anteriorly and suspending it by sutures to deter it from falling back in the oral cavity during sleep and vibrating or causing an occlusion in the airway. Other surgical measures have included removing a portion or portions of the tongue and/or other anatomical tissue or structures which can obstruct or restrict the patient's airway.

Surgical techniques have been proposed using standard surgical instruments, laser energy and RF energy. Although surgical measures are generally more effective than medications, the risks associated with surgery can be prohibitive and/or are often unacceptable to the patient. In addition, conventional surgery is associated with considerable trauma and pain for the patient as well as the potential for post-operative complications. Laser and RF energy ablation procedures are less invasive than surgery with instruments but are difficult to control; and, if too much tissue is ablated, severe consequences may ensue. Multiple ablation treatments are usually required in order to achieve the results desired, and each treatment may cause the patient to experience significant pain for a considerable length of time. Laser and RF energy ablation systems are not able to repeatedly and consistently produce a discrete lesion of definitive size. Physical measures to treat snoring disorders and/or sleep apnea syndrome include weight loss and the use of various appliances.

Ablation of the tongue to treat snoring disorders and/or obstructive sleep apnea syndrome is exemplified by U.S. Pat. Nos. 5,624,439, 5,707,349, 5,728,094, 5,730,719, 5,738,114, 5,743,904, 5,800,379, 5,807,308, 5,817,049 and 5,879,349 to Edwards. As noted above, U.S. Pat. Nos. 5,707,349, 5,728,094, 5,730,719, 5,800,379, 5,807,308, 5,817,049 and 5,879,349 disclose the use of RF electrodes to transmit electromagnetic energy to tissue to be ablated while merely alluding to ultrasound as a possible source of ablative energy. The electrodes are introduced within the tissue to effect ablation in the interior of the tissue.

Accordingly, the need exists for methods of tongue reduction by thermal ablation using high intensity focused ultrasound whereby the tongue of a patient can be reduced in volume, bulk or size, via elimination and/or alteration of the normal tissue, to reduce or eliminate vibration of the tongue and/or to increase the space or size of the patient's airway in a minimally invasive, bloodless procedure not requiring physical penetration of the tongue and while confining ablation to a specific target area or areas within the tongue.

SUMMARY OF THE INVENTION

Accordingly, it is a primary object of the present invention to overcome the various disadvantages of prior methods of tongue reduction.

It is also an object of the present invention to effect tongue reduction by thermal ablation using high intensity focused ultrasound.

Another object of the present invention is to utilize high intensity focused ultrasound to treat airway obstructions.

A further object of the present invention is to utilize high intensity focused ultrasound to treat snoring disorders.

An additional object of the present invention is to utilize high intensity focused ultrasound to treat obstructive sleep apnea syndrome.

It is also an object of the present invention to use high intensity focused ultrasound to thermally ablate the tongue without impairing tongue function.

Yet another object of the present invention is to use high intensity focused ultrasound to produce a lesion within tissue of the tongue while preserving the mucosa of the tongue.

The present invention has as a further object to use high intensity focused ultrasound to form a subsurface lesion in the tongue including relatively stiffer tissue to inhibit tongue vibration.

The present invention also has as an object to use high intensity focused ultrasound to ablate the tongue at an internal target area without physical penetration of the tongue by the member used to deliver the ultrasound energy.

Still a further object of the present invention is to focus ultrasound energy within the tongue to form an internal lesion beginning a predetermined distance beneath an external surface of the tongue.

The present invention also has as an object to focus ultrasound energy, emitted by an ultrasound emitting member, within the tongue to ablate tissue of the tongue at a target area beginning a predetermined distance from an active face of the ultrasound emitting member.

Some of the advantages of the present invention are that varying intensity levels of ultrasound energy can be delivered to tissue of the tongue for varying periods of time, the duration or time of high intensity focused ultrasound delivery or application to the tissue needed to accomplish a desired ablation may be relatively brief depending on desired lesion size and/or desired effect on the tissue, the transducer or other member used to emit the ultrasound energy may remain stationary or may be moved manually or automatically from one position or location to another on the tongue in order to ablate a target area, a plurality of individual target areas can be ablated with the positions or locations for the target areas selected such that the target areas, when ablated, cumulatively form a single lesion of desired size and/or shape, the transducer or other member can include a single transducer element or a plurality of transducer elements, the ultrasound emitting member can remain stationary while a transducer element or elements thereof is/are moved to scan a target area with focused ultrasound, the transducer or other member may be designed with a focusing configuration designed to ensure that the lesion begins a desired depth within the tissue and that the lesion has a desired depth, anatomical tissue of the tongue may be effectively removed to debulk or reduce the size, volume and/or configuration of the tongue, tissue of the tongue may be rigidified or stiffened via thermal damage thereto to reduce the volume of relatively softer, normal tongue tissue, tongue reduction is accomplished with minimal trauma and pain for the patient, the transducer or other member is positioned externally adjacent or in contact with an external surface of the tongue or is acoustically coupled with tissue of the tongue to form an internal lesion without damaging the external tissue surface and without formation of fistulas, no external wound is presented since the mucosa of the tongue is preserved, and a discrete lesion of definitive size can be repeatedly and consistently produced.

These and other objects, advantages and benefits are realized with the present invention as generally characterized in a method of tongue reduction by thermal ablation using high intensity focused ultrasound wherein an ultrasound emitting member is introduced in a patient's oral cavity and is positioned adjacent an external tissue surface of the tongue. Ultrasound energy is emitted from the ultrasound emitting member into the tissue of the tongue, and the ultrasound energy is focused within the tongue at one or more focusing zones at or within a target area disposed beneath the external tissue surface. Due to focusing of the ultrasound energy, the ultrasound energy is of higher or greater intensity in tissue at the one or more focusing zones than in tissue surrounding the target area. The high intensity ultrasound energy at the one or more focusing zones causes the tissue at the target area to be heated to an ablative temperature to create an internal lesion. Once a desired lesion or lesions has/have been formed in the tongue, the ultrasound emitting member is withdrawn from the patient's oral cavity. Depending on the characteristics of the lesion, all or some of the lesion may be degraded and absorbed by the patient's body such that the tongue is smaller in size than prior to treatment. Depending on the characteristics of the lesion, all or some of the lesion may remain as altered tissue, such as scar tissue that is stiffer, tighter or more rigid than the normal undamaged tongue tissue, the volume of normal undamaged tissue therefore being less than prior to treatment. Since the tongue is smaller in size and/or more stiff, the patient's airway is correspondingly larger in size and/or the tongue is less likely to vibrate so as to eliminate or alleviate various airway related disorders or conditions including airway obstructions, snoring disorders and sleep apnea syndrome.

The ultrasound emitting member has a focusing configuration causing the ultrasound energy to be focused a predetermined distance from an active face of the ultrasound emitting member and, therefore, from the external tissue surface, so that the mucosa of the tongue is preserved. Also, the focusing configuration results in formation of a lesion of predetermined or known depth, which is selected so that the lesion does not extend deeper than desired in the tissue. The location and arrangement of the one or more focusing zones in the tissue results in formation of a specific size lesion having a specific configuration. A single discrete lesion or a plurality of single discrete lesions can be formed in the tongue in a single procedure or treatment performed at one time or in multiple procedures or treatments performed at different times. Where a plurality of lesions are formed, the lesions can comprise lesion portions formed contiguous to one another so that the lesion portions together form or create a single lesion of larger size and/or of a desired configuration.

BRIEF DESCRIPTION OF THE DRAWINGS

FIG. 1 is a broken perspective view, partly schematic, illustrating a high intensity focused ultrasound ablation assembly for use in the methods of the present invention.

FIG. 2 is a broken bottom view of an ultrasound emitting member of a focused ultrasound ablation device of the high intensity focused ultrasound ablation assembly.

FIG. 3 is a broken side view, partly in section, of the ultrasound emitting member and depicting focusing of ultrasound energy in anatomical tissue to form a lesion.

FIG. 4 is a broken top view illustrating the surface configuration of the lesion of FIG. 3.

FIG. 8 is a broken side view, partly in section, illustrating use of the ultrasound emitting member of FIG. 3 to create a submucosal lesion in the tongue.

FIG. 9 is a broken anterior view illustrating a single submucosal lesion created in the tongue.

FIG. 11 is a broken anterior view illustrating the alternative lesion created in the tongue.

DESCRIPTION OF THE PREFERRED EMBODIMENTS

Figure 6:
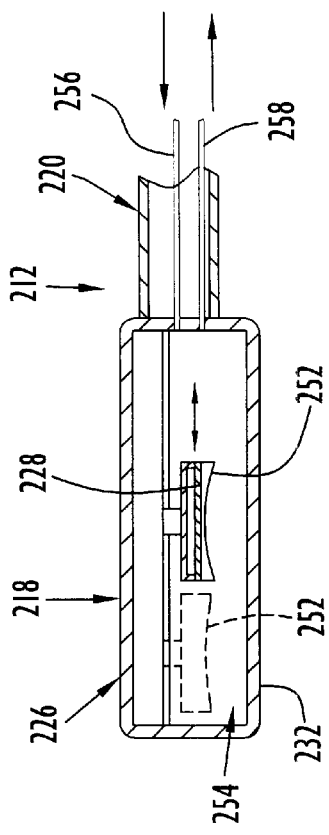
FIG. 6 is a broken side view, partly in section, of another alternative focused ultrasound ablation device for use in the methods of the present invention.

A high intensity focused ultrasound ablation assembly or system 10 for use in the methods of the present invention is illustrated in FIG. 1. The high intensity focused ultrasound ablation assembly 10 includes a focused ultrasound ablation device 12, a power supply 14 and a controller 16. The focused ultrasound ablation device 12 includes a focused ultrasound emitting member 18, an elongate handle shaft or body 20 having a distal end at which the ultrasound emitting member is disposed and a handle or handpiece 22 coupled to a proximal end of the handle shaft 20. As shown in FIGS. 2 and 3, the ultrasound emitting member includes a transducer 24 carried by or within a housing, carrier or case 26. The transducer, which includes one or more individual ultrasound emitting elements ortransducerelements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical current or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration causing the ultrasound energy generated thereby to be focused, as shown by arrows in FIG. 3, at focusing zones F, respectively.

The transducer elements 28 are arranged in an array on or in housing 26; and, therefore, the transducer 24 may be considered a multi-array transducer. In the case of ultrasound emitting member 18, the transducer elements are arranged in a planar array of five rows R and six columns C best shown in FIG. 2, although the transducer elements can be arranged in any number of rows and columns depending on the number of transducer elements provided in the ultrasound emitting member. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different.

The transducer elements 28 can be referenced by their location in the array. For example, the transducer element 28' in the first row, first column can be designated transducer element R1C1, the transducer element 28" in the first row, second column can be designated transducer element R1C2 and so on. The transducer elements of each row are disposed close to one another, and the transducer elements of each column are disposed close to one another such that there is minimal space between adjacent transducer elements. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external bottom surface 32 of housing 26. The piezoelectric elements are curved in a direction inwardly of surface 32 such that ultrasound energy generated by the piezoelectric elements is emitted from focused ultrasound emitting member 18 in a direction perpendicular or normal to surface 32 for focusing at the focusing zones F, which are spaced outwardly of surface 32. Accordingly, surface 32 is an active surface or face of the ultrasound emitting member which, when positioned externally on, adjacent or in contact with a mass, body or area of anatomical tissue A, results in the ultrasound energy emitted by the transducer being focused at zones F, which will be disposed within the anatomical tissue A as shown in FIG. 3. When the ultrasound emitting member is positioned on, against or adjacent the tissue A at a location aligned with a designated target area 34 within the tissue A, the focusing zones will be disposed at or within the target area as shown in FIG. 3.

Each focusing zone F consists of a single point or a plurality of points forming a zone at which the ultrasound energy is focused. Each focusing zone is in line with a central axis of the corresponding transducer element. Each focusing zone is disposed a fixed predetermined distance D from a plane containing the active face 32, the distance D for each focusing zone being perpendicular or normal to the active face 32. Therefore, the focusing zones F will also be disposed a predetermined perpendicular distance or a calculable or determinable perpendicular distance from an external tissue surface 36 of tissue A with which the active face 32 is placed in contact or adjacent thereto. Where the active face 32 is placed in contact with the external tissue surface 36, the perpendicular distance that zones F are disposed from external tissue surface 36 will be the same as the predetermined distance D as shown in FIG. 2. Where the active face 32 is not placed in contact with the external tissue surface 36 but, rather, is spaced from the external tissue surface 36 by a known amount, for example, the perpendicular distance that zones F are disposed from the external tissue surface will correspond to distance D minus the distance that the active face 32 is spaced from the external tissue surface 36. Where the active face 32 is spaced from the external tissue surface 36, an acoustic coupling medium can be disposed between the external tissue surface 36 and the member 18 as explained further below.

Since the ultrasound is focused at zones F, the ultrasound is of greater or higher intensity at focusing zones F and is thusly focused or concentrated at the focusing zones F, causing tissue A at the focusing zones F to be heated to an ablative temperature. When all of the transducer elements 28 are actuated, as shown in FIG. 3, heating of tissue A will occur at a focusing zone F for each transducer element. Since the transducer elements are disposed close to one another, the areas of tissue between the focusing zones are also heated to an ablative temperature due to thermal conduction causing the dispersal or spread of heat from the focusing zones. Accordingly, a discrete, definitive lesion 38 is formed in the tissue while the temperature of the tissue surrounding the lesion remains below damaging levels such that the surrounding tissue is undamaged and preserved. When all of the transducer elements 28 are actuated, a lesion of specific configuration and size is created within the body, mass or area of anatomical tissue A for the transducer 24 in accordance with the intensity level of the emitted ultrasound energy and the duration or time of ultrasound energy delivery to the tissue. Accordingly, a lesion having a specific length, width and depth is formed in the tissue. FIGS. 3 and 4 illustrate the lesion 38 formed in tissue A when all of the transducer elements are actuated. The lesion 38 has a generally rectangular configuration with a predetermined length and width dictated by the configuration of the array and a predetermined depth dictated by the length of the focusing zones. When the ultrasound emitting member 18 is positioned on, against or adjacent the tissue A at a location aligned with a designated target or lesion area 34 in the tissue, the lesion 38 will be formed at or coincide with the target area as shown in FIGS. 3 and 4.

The housing 26 can have various external configurations and sizes in accordance with the size, configuration and design of the transducer and the array in which the transducer elements are arranged including rectangular, square, circular, curved and cylindrical or tubular configurations. In the case of ultrasound emitting member 18, the housing 26 has a generally rectangular external configuration with rounded or blunt corners and/or edges to avoid damage to anatomical tissue. It should be appreciated that the transducer elements 28 can be disposed within the housing with the ultrasound energy generated by the transducer elements being transmitted or emitted through or from a wall of the housing, such wall being made of material through which ultrasound energy can pass and defining the active face for the ultrasound emitting member. Of course, a surface of the transducer can itself define the active face for the ultrasound emitting member.

The active face for ultrasound emitting member 18 is parallel to a longitudinal axis of member 18 so that the predetermined distance for zones F beyond the active face and the external tissue surface is perpendicular to the longitudinal axis. It should be appreciated that, depending on the design of the ultrasound emitting member, the predetermined distances for the focusing zones beyond the active face and the external tissue surface can be perpendicular to the active face but non-perpendicular to the longitudinal axis. The active face may be rigid or flexible or deformable depending on procedural use. The active face and/or the transducer may be designed to conform to the shape of the tissue surface against which the active face is placed. Of course, where soft tissue is being ablated, the soft tissue may conform to the shape of the active face and/or the transducer where the active face and/or the transducer is/are more rigid than the tissue.

The handle shaft 20 comprises an elongate, hollow or tubular member of sufficient length to position the ultrasound emitting member 18 at various operative sites in or on the body of a patient while the handle 22 is maintained at a remote location, typically externally of the patient's body. Preferably, the handle shaft 20 is malleable as disclosed in the application entitled Focused Ultrasound Ablation Devices Having Malleable Handle Shafts and Methods of Using The Same, the disclosure of which is incorporated herein by reference. The distal end of handle shaft 20 is coupled with the ultrasound emitting member by being disposed on or within an end wall of housing 26 or by extending through the end wall of housing 26 to be disposed within the housing.

The handle 22 has a forward end coupled to the proximal end of handle shaft 20 and has a rearward end. The handle 22 preferably has a configuration to facilitate grasping by a surgeon or other operator. In the case of focused ultrasound ablation device 12, the handle 22 has a cylindrical body with raised, external annular segments 40. The segments 40 are longitudinally spaced from one another, and one or more controls or switches 42, such as push button controls or switches, may be disposed on handle 22 between spaced segments 40. The one or more controls or switches 42, where provided, may be used to effect operation of the focused ultrasound ablation device. It should be appreciated that the handle can be provided without controls or switches in which case operation of the focused ultrasound ablation device may be effected by one or more controls or switches located on the power supply, the controller and/or a dedicated structure such as a foot pedal. Where the one or more controls or switches are provided on the handle, as illustrated for focused ultrasound ablation device 12, the one or more controls or switches is/are desirably placed at a location on the handle amenable to convenient operation thereof by the hand of the surgeon or other operator grasping the handle. As shown in FIG. 1, the push button controls or switches 42 are accessible and operable by a finger of a hand grasping the handle 22 for one-handed operation of ablation device 12.

The proximal end of handle shaft 20 is coupled with handle 22 at the forward end thereof and, in particular, at a forward wall of the handle. The proximal end of handle shaft 20 may be disposed on or within the forward wall or may extend through the forward wall to be disposed within the handle 22. With the proximal end of the handle shaft thusly coupled to the handle, the longitudinal axis of the handle is coaxially aligned with the longitudinal axis of the handle shaft at the proximal end thereof. The shaft and the handle are preferably made of a material or materials that does/do not transmit ultrasound energy to the surgeon or other operator.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle.

In the case of focused ultrasound ablation device 12, a transmission wire 44 is provided for each piezoelectric element and, therefore, for each transducer element. As shown in FIG. 3, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to transducer so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other selected transducer elements can remain deactivated to prevent transmission of electrical current thereto when the power supply is actuated or switched to an "on" mode. It should be appreciated that various components and/or methodology can be incorporated in the device 12, including the power supply 14 and/or the controller 16, to permit selective actuation of selected ones of the transducer elements 28 and that such components and/or methodology would be within the purview of one skilled in the art.

Figure 5:
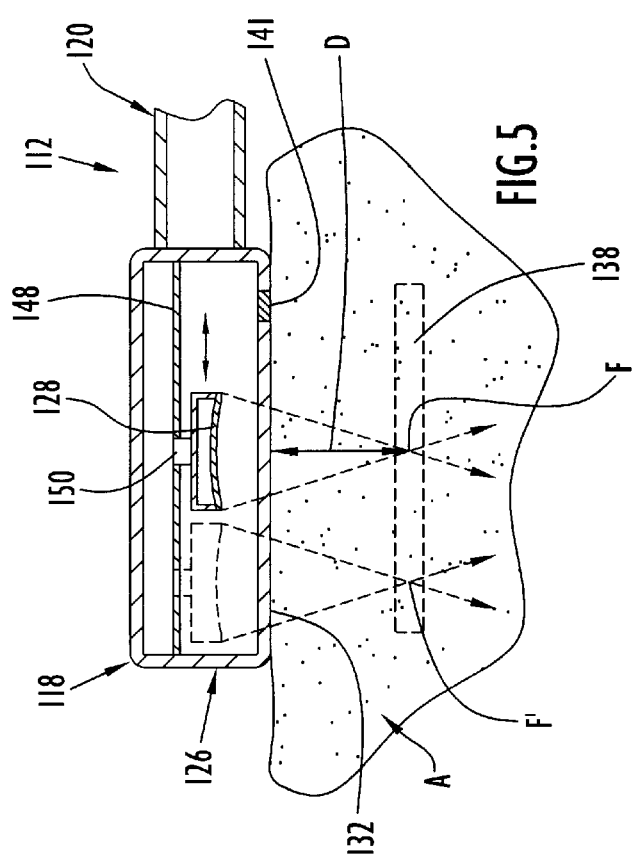
FIG. 5 is a broken side view, partly in section, of an alternative focused ultrasound ablation device for use in the methods of the present invention and depicting formation of a lesion using the alternative focused ultrasound ablation device.

An alternative focused ultrasound ablation device 112 for use in the methods of the present invention is illustrated in FIG. 5. The focused ultrasound ablation device 112 is similar to device 12 and includes ultrasound emitting member 118 carried by handle shaft 120. As shown in FIG. 5, the ultrasound emitting member 118 for device 112 includes a single transducer element 128 disposed within housing 126 and being capable of generating and emitting ultrasound energy in response to being supplied with electrical power from the power supply. The transducer element 128 includes a piezoelectric element that vibrates to produce ultrasound energy when electrical current is supplied thereto. The piezoelectric element is electrically coupled to the power supply during use, such as via a transmission wire (not shown) and has a concave configuration causing the ultrasound energy generated thereby to be focused, as shown by arrows in FIG. 5, at a focusing zone F located fixed distance D from an active face 132 of housing 126.

The housing 126 has a generally rectangular configuration with a lower or bottom wall 132 thereof defining the active face for member 118. The transducer element 128 is disposed in housing 126; however, the transducer element can be carried externally on the housing and/or can partly or entirely form or define the bottom wall of the housing. The piezoelectric element for transducer element 128 is movably supported on a platform 148 in housing 126. The platform 148 is parallel to active face 132, and both the platform and active face are planar. The piezoelectric element is curved in a direction away from active face 132 such that ultrasound energy generated thereby passes through active face 132 for focusing at the focusing zone F, the active face or housing bottom wall being made of a material through which ultrasound energy can pass. Accordingly, when the bottom wall of housing 126 is positioned externally adjacent or in contact with a mass, body or area of anatomical tissue A, the ultrasound energy emitted by transducer element 128 is focused at zone F, which will be disposed within the anatomical tissue A as shown in FIG. 5.

The piezoelectric element is supported on a base member 150 which rides along tracks in or on platform 148. The base member can include a motor, or a motor can be mounted elsewhere in the device 112, for moving the base member and, therefore, the piezoelectric element, along the tracks. The tracks, which can be formed by grooves in the platform receiving a tongue of the base member, extend lengthwise and widthwise in a grid pattern along the platform. The platform has a length and width the same as or substantially the same as the length and width of the interior of the housing. Accordingly, the piezoelectric element is movable longitudinally, i.e. lengthwise, in forward and rearward directions in the housing as shown by an arrow in FIG. 5. Also, the piezoelectric element is movable transversely, i.e. side to side, in the housing in a direction perpendicular to the arrow.

By selecting and controlling, via the controller, the range of movement of the transducer element 128 in the longitudinal and transverse directions, a scanning effect is obtained by which the focusing zone F is moved within the tissue while the member 118 remains stationary and does not move relative to the tissue. For example, the transducer element 128 is illustrated in dofted lines in FIG. 5 moved longitudinally, forwardly to produce a focusing zone F' forwardly of focusing zone F. By "firing" the transducer element to emit ultrasound energy as it is moved longitudinally and/or transversely, a designated target area in the tissue can be scanned with focused ultrasound energy so that the tissue is heated to an ablative temperature at various focusing zones throughout the target area to form a lesion, such as lesion 138. Also, by selecting and controlling the range of movement of the piezoelectric element in the longitudinal and transverse directions via the controller, which directs the motor to move the transducer element the selected range, a lesion of desired size and configuration is obtained. Accordingly, transducer element 128 can be used to form lesions of various sizes and shapes. The bottom wall 132 may be rigid or flexible or deformable depending on procedural use and may be formed as a flexible membrane. Where the bottom wall 132 is flexible or deformable, the active face is capable of conforming to the shape of the tissue surface against which it is placed. Of course, where soft tissue is being ablated, the soft tissue will confirm to the shape of the active face where the active face is more rigid than the soft tissue.

The ultrasound emitting member 118 can include a temperature sensor 141, such as a thermocouple, for sensing the temperature at the transducer/tissue interface. The temperature sensor can be disposed on or in the housing, can be disposed externally of the housing or can be disposed on, in or externally of the transducer. Depending on the design of the temperature sensor, the temperature sensor may penetrate the tissue slightly. The temperature sensor 141 is embedded in the bottom wall of the housing. During use, the temperature sensor 141 detects the temperature of the tissue at the transducer/tissue interface, i.e. the junction of the active face with the external tissue surface. The controller can be programmed to effect automatic shut down of the ablation device 112 when the temperature sensed by the temperature sensor reaches or exceeds a predetermined temperature. The predetermined temperature can be selected by the surgeon or other operator and provided as input to the controller. By automatically terminating ultrasound energy delivery to the tissue when a preselected temperature at the transducer/tissue interface is reached or exceeded, mucosal damage and fistula formation are avoided.

It should be appreciated that the focused ultrasound ablation devices can be provided with imaging capabilities for visualizing operative sites at which the focused ultrasound ablation devices are to be used, for visualizing guidance and/or positioning of the ultrasound emitting members at the operative sites and/or for examination and diagnosis. The focused ultrasound ablation devices can thusly be used for both therapy and imaging, and observation of a detected image can be obtained at a location remote from the operative site. For example, the ultrasound emitting members can be provided with ultrasound imaging transducers as described in the patent application incorporated herein by reference and entitled Methods of Soft Palate Reduction By Thermal Ablation Using High Intensity Focused Ultrasound.

Alternatively or in addition to imaging transducers, conventional optical guidance mechanisms, such as fiber optic mechanisms, can be used to provide remote visualization, and such optical guidance mechanisms can be separate from or formed as part of the focused ultrasound ablation devices. The focused ultrasound ablation devices or assemblies can be provided with viewing devices such as eyepieces on the shafts or the handles or video monitors for viewing images of the operative sites from the remote locations, typically externally of the patients' bodies. The focused ultrasound ablation devices or assemblies can be designed in various ways to provide for ultrasonic and/or fiberoptic imaging capabilities and may incorporate the various apparatus or systems disclosed in U.S. Pat. Nos. 33,590, 4,658,828, 4,858,613, 4,955,365, 5,036,855, 5,080,101, 5,080,102, 5,117,832, 5,143,074, 5,150,711, 5,150,712, 5,354,258, 5,431,621, 5,520,188, 5,676,692, 5,762,066, 5,882,302 and 5,895,356.

FIG. 6 illustrates another alternative focused ultrasound ablation device 212 having a transducer element 228 operated in a manner similar to transducer element 128 so that the transducer element 228 is movable longitudinally as shown in dotted lines and by the arrow in FIG. 6 as well as transversely as described for transducer element 128. The transducer element 228 is formed by a flat or planar piezoelectric element and a concave lens 252 that focuses ultrasound energy produced by the piezoelectric element at a focusing zone, similar to that for transducer element 128, located a predetermined perpendicular distance from the active face 232. The piezoelectric element is electrically coupled to the power supply during use, such as via a transmission wire (not shown). The lens 252 is made of ultrasound transmitting material and has a specific focusing configuration or geometry to obtain focusing of the ultrasound energy at a focusing zone, similar to that for transducer element 128, located a predetermined distance from the active face. A space or cavity 254 is defined in the housing 226 around the transducer element 228. The handle shaft 220 has inlet and outlet conduits 256 and 258, respectively, extending therethrough. The inlet conduit 256 communicates or is coupled with a source or supply of cooling medium, such as cooling fluid, adapted to be introduced or pumped therethrough. The inlet and outlet conduits 256 and 258 communicate with the space 254 such that the cooling medium carried by the inlet conduit enters the space and is positively or actively withdrawn from or is passively forced from the space through the outlet conduit. In this manner, a cooling medium such as water can be introduced into and withdrawn from the housing 226, which can be fluidically sealed, in order to dissipate heat in the housing and effect cooling of the ultrasound emitting member 218 including cooling of the active face. In this manner, cooling of the external tissue surface and, in particular, the mucosal surface, is effected to further avoid damage to the mucosa and reduce the risk of fistula formation.

Figure 7:
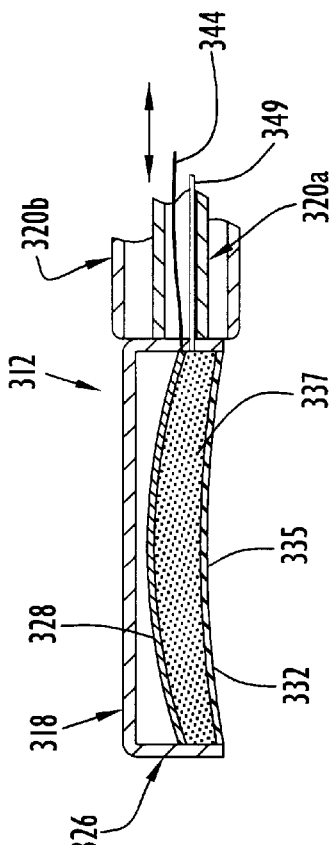
FIG. 7 is a broken side view, partly in section, of a further alternative focused ultrasound ablation device for use in the methods of the present invention.

A further alternative focused ultrasound ablation device for use in the methods of the present invention is illustrated in FIG. 7 at 312 and includes an ultrasound emitting member 318 that is representative of an ultrasound emitting member wherein the transducer is acoustically coupled to the tissue via a coupling medium. The ultrasound emitting member 318 is also representative of an ultrasound emitting member that is mechanically moved to linearly scan a target area with high intensity focused ultrasound. The ultrasound emitting member 318 is disposed at the distal end of an inner handle shaft 320*a*, which is movably disposed in an outer handle shaft 320*b*. The member 318 includes transducer element 328 formed by a curved piezoelectric element disposed in housing 326, the bottom wall 332 of which is formed by a membrane 335, which can be resilient, flexible or elastic. A transmission wire 344 extends through inner shaft 320*a* and is connected to the piezoelectric element for electrically coupling the piezoelectric element with the power supply. An acoustic coupling medium such as an acoustic fluid or gel 337 capable of transmitting ultrasound occupies the space between the membrane and the piezoelectric element. The coupling medium can be introduced in and removed from the housing, which can be fluidically sealed, via a conduit 349 extending through inner shaft 320*a* and communicating with the space between the membrane and the piezoelectric element.

Ultrasound energy produced by the piezoelectric element in response to electrical excitation thereof propagates or passes through the coupling medium, which acoustically couples the transducer element to anatomical tissue positioned in contact with the membrane. The membrane has a somewhat curved shape conforming to the curvature of the tongue; however, the membrane may be capable of flexing or deforming as described in the application incorporated herein by reference and entitled Methods of Soft Palate Reduction By Thermal Ablation Using High Intensity Focused Ultrasound. The ultrasound emitting member 318 is representative of an ultrasound emitting member wherein the coupling medium is formed as part of the ultrasound emitting member. It should be appreciated, however, that the coupling medium can be provided in a device separate from the ultrasound emitting member and interposed between the anatomical tissue and the ultrasound emitting member.

The inner shaft 320a is reciprocatively movable longitudinally, forwardly and rearwardly, relative to and within the outer shaft 320b to control the extension of member 318 distally from or beyond the outer shaft. Accordingly, the member 318 can be retracted and extended relative to the outer shaft to protrude or extend a desired extension distance from or beyond the outer shaft, the member 318 being illustrated in FIG. 7 fully exposed from the outer shaft. The handle for focused ultrasound ablation device 312 can be provided with a motor or other mechanism for moving the inner shaft longitudinally relative to the outer shaft. Longitudinal extension of the member 318 can begin with the member 318 fully exposed from the outer shaft or disposed partly or entirely within the outer shaft, the member 318 being accommodated in the outer shaft. As the member 318 is extended relative to the outer shaft while the transducer element 328 is "fired" to emit ultrasound energy, tissue adjacent the active face is scanned with high intensity focused ultrasound, and a similar effect is achieved when the member 318 is retracted from an extended position. In this manner, the focusing zone for the piezoelectric element is moved linearly within the tissue to cause heating of a designated target area and formation of a subsurface lesion of desired size and shape, the size and shape being dictated by the range of movement or reciprocative stroke for member 318. The device 312 can be programmed via the controller to obtain a desired lesion by selecting the appropriate extension distance and/or reciprocative stroke for the ultrasound emitting member.

Various transducers can be used in the methods of the present invention. An individual transducer can include a single piezoelectric or other transducer element, an annular array of such elements, a linear array of such elements, and/or a curved linear array of such elements. More than one transducer can be provided in a single ultrasound emitting member. The piezoelectric elements can be made of various piezoelectric materials such as PZT crystal materials, hard lead, zirconate/lead titanium piezoelectric ceramic, or lithium-niobate piezoceramic material. The transducer elements can be of various sizes and can have various focusing geometries. Exemplary transducers that may be used or modified for use in the methods of the present invention are disclosed in U.S. Pat. Nos. 4,858,613, 4,955,365 and 5,036,855 to Fry et al, U.S. Pat. No. 5,117,832 to Sanghvi et al, U.S. Pat. Nos. 5,492,126 and 5,520,188 to Hennige et al, U.S. Pat. No. 5,676,692 to Sanghvi et al and U.S. Pat. No. 5,762,066 to Law et al, the disclosures of which are incorporated herein by reference. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of anatomical tissue to be effected in response to the application or delivery of ultrasound energy to the tissue for a relatively short duration or length of time. In accordance with the present invention, the duration or length of time for ultrasound energy delivery or application to the tissue preferably ranges from 2 to 45 seconds depending on desired lesion size and/or ablative effect.

In accordance with the methods of the present invention, high intensity focused ultrasound is used to ablate a target area within tissue of the tongue to create an internal ablative lesion. Depending on the characteristics of the lesion, such as the dimensions of the lesion, the severity of tissue damage and/or the nature of the ablated tissue, all or part of the lesion may be naturally degraded and absorbed by the patient's body or may remain as altered tissue, such as scar tissue that is more stiff or firm than the untreated tissue. Accordingly, the lesion may be entirely absorbed, may remain entirely as scar tissue, or may be partly absorbed and partly remaining as scar tissue. Where the lesion is partly or entirely absorbed, the tongue shrinks or decreases in size resulting in increased airway space. In this manner, the size or volume of the tongue can be reduced and/or the configuration of the tongue can be changed in order to treat airway associated disorders or conditions including airway obstructions, snoring disorders and/or sleep apnea syndrome in patients. Where the lesion remains partly or entirely as scar tissue, the scar tissue, being stiffer, firmer or more rigid than normal undamaged tissue, is more resistant to vibration or resonance thereby alleviating or eliminating snoring disorders and/or sleep apnea syndrome. In addition, the scar tissue may contract, thusly reducing the size of the tongue and correspondingly increasing the size of the airway to alleviate or eliminate airway obstructions. It should be appreciated that regardless of whether the lesion is absorbed and eliminated or remains as altered tissue, partly or entirely, the tongue is nonetheless "reduced". Accordingly, as used herein, "reduction" of the tongue involves elimination or reduction of normal tongue tissue by absorption of ablated tissue and/or by transformation of normal undamaged tissue into altered tissue such as scar tissue.

The tongue T, as shown in FIG. 8, is a muscular soft tissue structure that runs from the posterior-inferior section of the oral cavity or mouth M, which forms part of airway W, to the opening of the oral cavity or mouth M. Its base or root B is directed backward and is connected with the os hyoides, the epiglottis, the soft palate and the pharynx. Its apex or tip is directed forward against the lower incisor teeth. An external mucous membrane, or mucosa, invests the entire extent of the free surface of the tongue and defines an external tissue surface 36. Underlying or beneath the mucous membrane or mucosa, the tongue is comprised of submucous muscular fibers, interposed fat, vessels and nerves. The size and thickness of the tongue varies from person to person but is thickest at its base. The tongue T can contribute to airway related disorders or conditions such as airway obstructions, snoring disorders and/or obstructive sleep apnea due to its thickness, size and/or shape or configuration in relation to other anatomical tissue or structures of the airway as well as due to vibration. In accordance with the present invention, high intensity focused ultrasound is used to debulk or reduce the size or volume of the tongue and thereby increase the size of the airway W and/or rigidify the tongue to resist vibration.

As shown in FIG. 8, the ultrasound emitting member 18 is introduced through the opening of the mouth or oral cavity M of a patient and is guided by the surgeon or other operator via manual manipulation of shaft 20 or its handle to position the active face 32 adjacent or in contact with the external tissue surface or mucosa 36 of the tongue T. The active face is placed at or on the tissue surface at a location aligned with a desired target area in the tissue. Also, all or specific ones of the transducer elements are selected for actuation or "firing" in accordance with the size and configuration of a lesion desired to be formed at the target area. The device 12 is programmed via the controller to effect actuation or "firing" of the selected transducer elements when electric current or a signal is supplied to the transducer. Of course, selection and programming for actuation or "firing" of selected transducer elements can be performed prior to introduction of member 18 in the oral cavity.

The shaft 20 is guided between the tongue T and the roof of mouth M, which forms part of airway W, and the tongue T can be depressed, as necessary, to facilitate introduction and positioning of the ultrasound emitting member 18 at the desired location. Positioning of the ultrasound emitting member 18 externally adjacent or in contact with the external tissue surface 36 of the tongue is facilitated by the configuration of shaft 20, which may correspond to the curvature of the airway W from the anterior of mouth M to the base of tongue T, or by the flexibility of the shaft 20 where the shaft 20 is resilient, malleable or otherwise non-rigid. Where the ultrasound emitting member is provided with the capability for imaging, guidance of the ultrasound emitting member through the airway W and proper positioning of the active face at the desired location on the tongue T can be visualized from a remote location, typically externally of the patient's body. In this manner, proper placement of the active face at the desired location can be visually confirmed. Where the ultrasound emitting member is not provided with the capability for imaging, a remote viewing device such as a conventional fiber optic scope can be introduced in the airway W, typically mouth M, to provide visualization. Of course, where the location on the tongue can be directly visualized by the surgeon, extraneous visualization aids may not be needed.

In the procedure illustrated in FIG. 8, the active face 32 is positioned in contact with the external tissue surface 36 at a location on the base of tongue T that is centrally or substantially centrally disposed between the sides of tongue T. The location on the tongue at which the active face is placed is in alignment with a desired site or target area within the tongue for creation of a lesion. Once the active face is positioned in contact with the tissue of the tongue at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the tongue at the corresponding focusing zones. In the illustrated procedure, all of the transducer elements are "fired" so as to emit ultrasound energy, except for the transducer elements R1C1, R1C2, R1C5, R1C6, R2C1, R2C6, R3C1, R3C6, R4C1, R4C6, R5C1, R5C2, R5C5 and R5C6. As a result thereof, anatomical tissue at the target area is heated to an ablative temperature causing a subsurface, submucosal or internal ablative lesion 238 to be formed in the tongue T, as shown in FIG. 8, while the ultrasound emitting member 18 remains external of and does not physically penetrate the tongue. The tissue at the target area is heated to an ablative temperature in the range of 60 to 100 degrees Celsius for the time required to achieve tissue ablation while the tissue surrounding the target area is not heated to damaging levels. The temperature to which the tissue of the target area is heated is sufficient to cause cell necrosis in the target area. The lesion 238 has a length, width and depth of known parameters depending on the locations of the selected transducer elements, the intensity of the ultrasound energy, the length of the focusing zones, the temperature to which the tissue is heated and the duration of energy delivery or application to the tissue.

Due to the predetermined distance D and the known length of the focusing zones, the lesion 238 begins at a beginning or starting margin 264 located a predetermined or known depth beneath or below the external tissue surface 36 and ends at an ending margin 266 located a predetermined or known depth beneath the external tissue surface 36, the distance between the beginning and ending margins corresponding to the depth of the lesion. By selecting the appropriate focusing zone depth, a desired thickness or depth of tissue between the beginning margin 264 and the external tissue surface 36 is disposed outside the target area and is therefore undamaged and preserved. In a preferred method, a 2 mm thick or an approximately 2 mm thick layer of tissue from the external tissue surface 36 to the beginning or starting margin 264 of the lesion 238 is preserved or undamaged thusly preserving the mucosa of the tongue T. Accordingly, there is a perpendicular distance of 2 mm or approximately 2 mm from the external tissue surface 36 to the beginning or starting margin 264 of the lesion. The lesion 238 has a depth of 5 mm or approximately 5 mm in the direction perpendicular to tissue surface 36 such that the lesion terminates or ends at the ending margin 266 disposed a depth of 7 mm or approximately 7 mm beneath the external surface 36 at the transducer/tissue interface. Accordingly, there is a perpendicular distance of 7 mm or approximately 7 mm from the external tissue surface to the ending margin 266 of the lesion. By selecting the appropriate focusing zone length, the depth of the ending margin 266 within the tissue is controlled thusly ensuring that the lesion 238 does not extend deeper than desired.

As shown in FIG. 9, the lesion 238 has a continuous or solid surface configuration or area of generally circular shape with a diameter of 10 mm or approximately 10 mm, the procedure of FIGS. 8 and 9 being representative of a single treatment procedure. Although the diameter or other external dimensions, such as length and width, of the lesion can be determined by the locations of the "fired" transducer elements, it should be appreciated that the diameter or length and/or width of the lesion can alternatively be obtained by manually moving the member 18 from site to site on the tongue as described further below.

Depending on the desired lesion size and/or ablative effect, ultrasound energy will be applied to the tissue for a duration in the range of 2–45 seconds. The emission of ultrasound energy by ultrasound emitting member 18 is terminated by the surgeon or other operator once a desired lesion size or amount of tissue ablation has been obtained, and the member 18 is withdrawn from the patient's oral cavity. Confirmation of lesion size can be obtained via ultrasound imaging of the tongue. FIG. 9 illustrates the oral cavity subsequent to withdrawal of member 18 therefrom. Lesion size is dictated by the configuration of the transducer, by selection of specific transducer elements for activation, and/or by moving the transducer from position to position on the tissue as explained further below. In order to terminate the emission of ultrasound energy by the ultrasound emitting member, the power supply is deactivated or switched to an "off" mode so that electrical current is no longer supplied to the selected piezoelectric elements.

The lesion 238, which contains thermally damaged or necrotized tissue, may be naturally degraded and absorbed, partially or entirely, by the patient's body such that the remaining tongue T will be smaller in bulk, size or volume than it was prior to treatment. Accordingly, the patient's airway W will be larger in size than it was prior to treatment thusly eliminating or alleviating airway related conditions or disorders such as airway obstructions, snoring disorders and sleep apnea syndrome. The lesion 238 may remain, partly or entirely, as relatively stiffer or firmer scar tissue such that a lesser amount of relatively softer, normal tongue tissue remains, whereby the tongue is of increased resistance to vibration or resonance thusly eliminating or alleviating snoring disorders and sleep apnea syndrome.

In the procedure described and illustrated above, the ultrasound emitting member is placed against the tongue at a desired location to form a lesion of final size and configuration in the tongue with focused ultrasound energy generated and emitted by the ultrasound emitting member without moving the ultrasound emitting member from the desired location. It should be appreciated, however, that where the lesion capable of being formed in the tongue with the ultrasound emitting member is smaller than the final size and/or different from the final configuration desired for the lesion, the ultrasound emitting member can be manually moved from location to location on the tongue to form a lesion of desired final size and configuration as explained further below.

Figure 10:
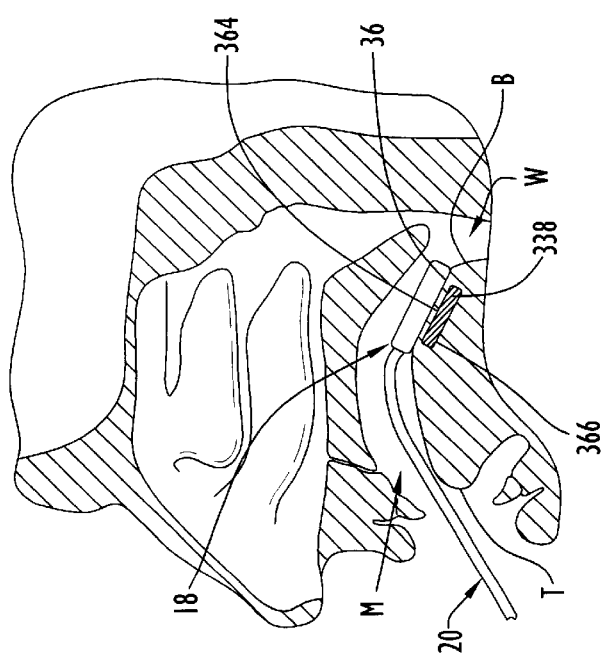
FIG. 10 is a broken side view, partly in section, illustrating formation of an alternative submucosal lesion in the tongue.

FIG. 10 illustrates formation of an alternative lesion 338 in tongue T using ultrasound emitting member 18 and "firing" all of the transducer elements, except for the transducer elements of the first column, to produce a square or substantially square lesion 338 having a length of 18 mm or approximately 18 mm, a width of 18 mm or approximately 18 mm and a depth of 6 mm or approximately 6 mm. As shown in FIGS. 10 and 11, the starting margin 364 for lesion 338 is located 4 mm or approximately 4 mm beneath the external tissue surface 36, and the ending margin 366 for lesion 338 is located 10 mm or approximately 10 mm beneath the external tissue surface 36. The shaft 20 is used to position the active face in contact with the external tissue surface at a central location on the base B of tongue T so that the lesion 338 is centrally located between the sides of tongue T as shown in FIG. 11. Subsequent to formation of lesion 338, it can be seen in FIG. 11 that the beginning and ending margins conform to the natural shape of the tongue.

Figure 12:
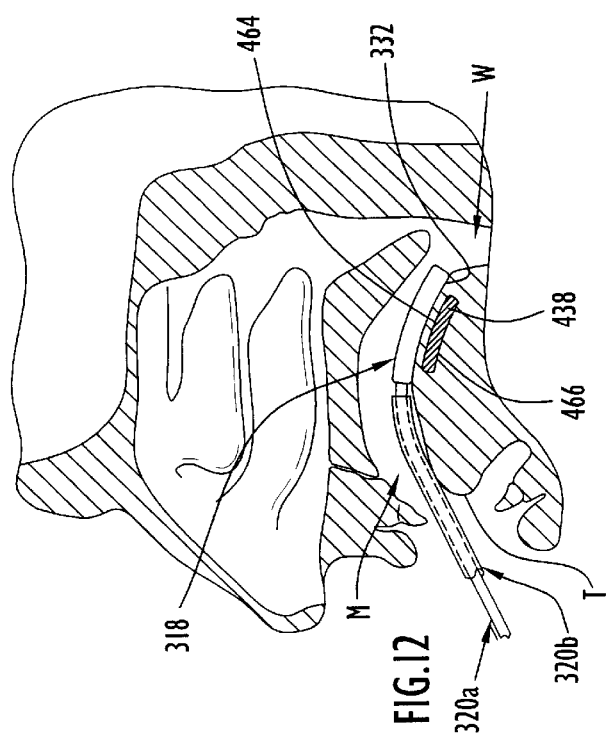
FIG. 12 is a broken side view, partly in section, illustrating use of the focused ultrasound ablation device of FIG. 7 to create another alternative submucosal lesion in the tongue.
Figure 13:
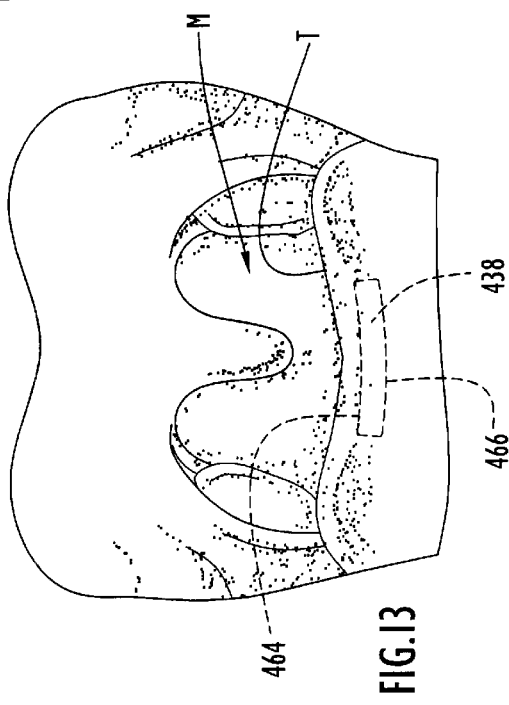
FIG. 13 is a broken anterior view illustrating the another alternative lesion created in the tongue.

FIG. 12 illustrates formation of another alternative lesion 438 using the ultrasound emitting member 318. The active face 332 of member 318 is positioned in contact with the external tissue surface 36 at the base B of tongue T. In particular, the external surface of the membrane is placed in contact with the external tissue surface 36 and conforms to the shape of the tissue surface. The member 318 is mechanically reciprocated a preselected stroke or range as ultrasound is generated and emitted by the transducer element. As a result thereof, a preselected target area is scanned with focused ultrasound energy and is heated to an ablative temperature to form submucosal lesion 438 in tongue T. The stroke or range of reciprocative movement selected for member 318 results in formation of a generally rectangular lesion 438 having starting margin 464 disposed 4 mm or approximately 4 mm below tissue surface 36, a length of 36 mm or approximately 36 mm extending longitudinally along tongue T, a width of 25 mm or approximately 25 mm and a depth of 6 mm or approximately 6 mm. As shown in FIG. 13, the lesion 438 is centrally located between the sides of tongue T. The ultrasound emitting member 318 allows lesion 438 to be formed in the tongue T in a single treatment or procedure and without the surgeon having to manually move the member 318 from site to site on the tongue. However, it should be appreciated that the lesion 438 can be formed in separate, multiple treatments or procedures or in a single treatment or procedure with or without manually moving the ultrasound emitting member from site to site on the tongue.

Figure 14:
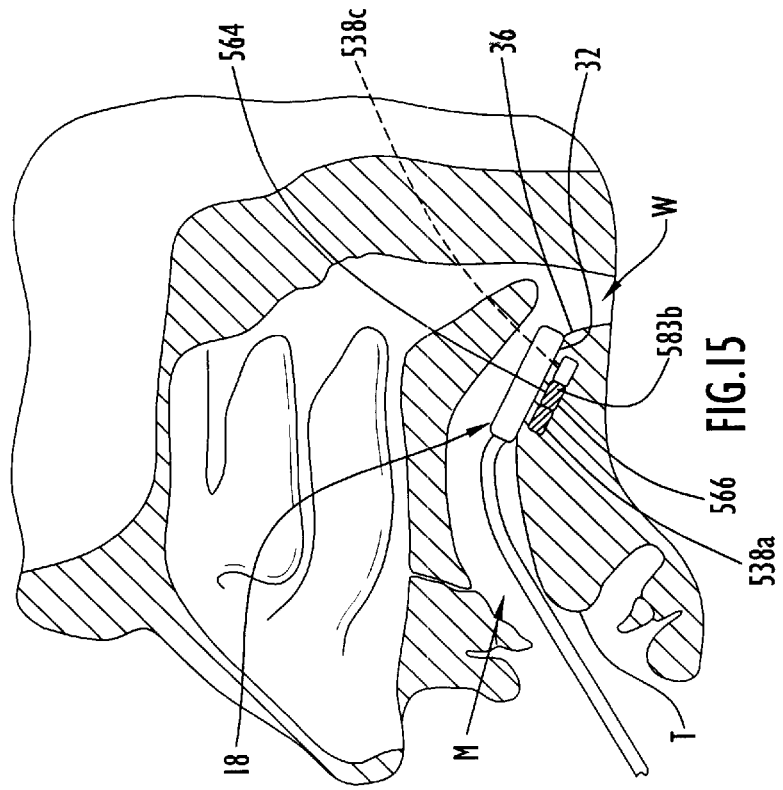
FIG. 14 is a broken side view, partly in section, illustrating use of the ultrasound emitting member of FIG. 3 to create a first lesion portion in the tongue.
Figure 15:
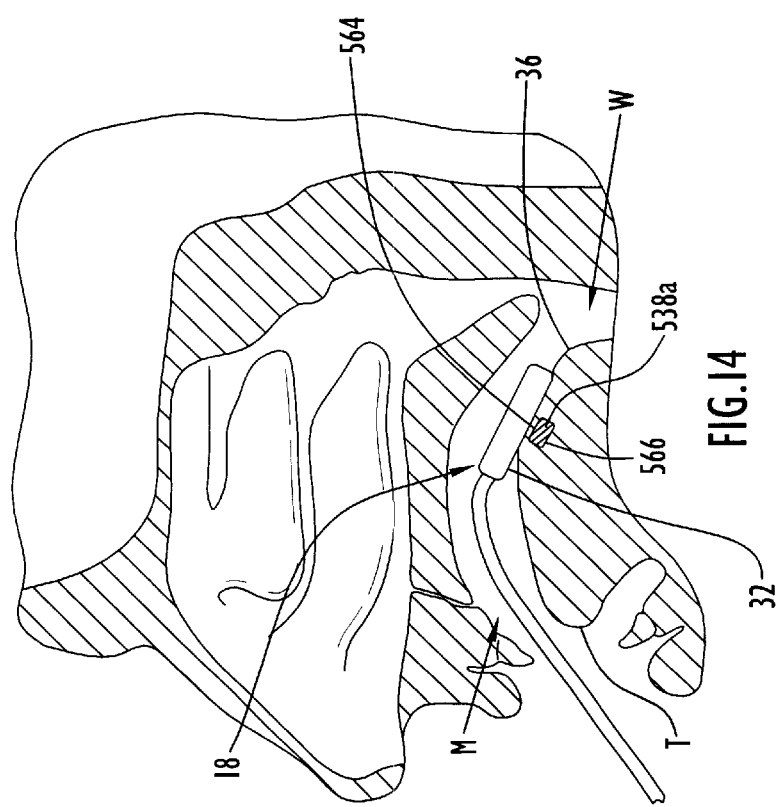
FIG. 15 is a broken side view, partly in section, illustrating use of the ultrasound emitting member of FIG. 3 to create second and third lesion portions in the tongue such that the first, second and third lesion portions together form a single lesion.

FIGS. 14 and 15 illustrate another method of tongue reduction by thermal ablation according to the present invention using the ultrasound emitting member 18. The method illustrated in FIGS. 14 and 15 is representative of a method or procedure wherein a plurality of discrete lesions are formed in tissue contiguous with one another in order to create a single, larger size lesion of desired final size and/or configuration. As shown in FIG. 14, the active face 32 is positioned in contact with the external surface 36 of the tongue T at a desired first location. Ultrasound energy emitted by selected transducer elements is used to form a first, submucosal, subsurface or internal lesion 538*a* at a first target area within the tissue. The lesion 538*a* begins or starts at the beginning margin 564 located below the external surface 36 and terminates at the ending margin 566, the lesion 538*a* having a depth between the beginning and ending margins and having a length and width dictated by the locations of the selected transducer elements. In order to form a lesion having a length and/or width larger than that for lesion 538*a*, the ultrasound emitting member 18 is manually moved from location to location on the external surface 36 to form a plurality of contiguous, individual lesions which together form a single lesion of larger, final size and/or a different configuration.

As shown in FIG. 15, the ultrasound emitting member 18 is manually moved distally or forwardly to be disposed further posteriorly in the airway W to position the active face 32 on the tissue surface 36 of the tongue at a second location further posteriorly of but in line with the first location. The selected transducer elements are used to emit ultrasound energy to form a second lesion 538*b* at a second target area that is adjacent, contiguous or in abutment with the first target area. The transducer elements can be actuated or "fired" while the member 18 is being moved from the first location to the second location to obtain a "scanning" effect, or the transducer elements can be actuated or "fired" after the member 18 has been moved to the second location. The second lesion 538*b* is created in the tissue contiguous, in abutment and continuous with the first lesion 538*a*. The second lesion starts or begins at the beginning margin 564 beneath the external tissue surface and terminates at the ending margin 566. The lesion 538*b* has a length and width the same as or substantially the same as the length and width for the lesion 538*a*. Accordingly, the lesions 538*a* and 538*b*, which may be considered first and second lesion portions, together form a single, discrete lesion having a length larger than the individual lengths of the lesion portions and a width corresponding to the width of the lesion portions. Yet a larger size, individual lesion can be formed in the tissue by manually moving the ultrasound emitting member 18 further distally or forwardly to be disposed further posteriorly in the oral cavity and positioning the active face at a third location on the tissue surface in line with the second location and in alignment with a third target area contiguous to the second target area. A third lesion or lesion portion 538*c* is created at the third target area as shown in dotted lines in FIG. 12, the third lesion or lesion portion 538*c* merging or being contiguous with the second lesion portion 538*b*. In this manner, a single, discrete lesion of increased length can be created in the tissue with the single, discrete lesion being formed by the individual lesion portions 538*a*, 538*b* and 538*c*.

In the procedure illustrated in FIG. 15, the ultrasound emitting member is manually moved longitudinally to create a final lesion having a length corresponding to the combined lengths of the individual lesion portions. It should be appreciated that the ultrasound emitting member can be manually moved laterally or transversely for positioning on the tissue in side by side relation with a previously formed lesion portion to create a lesion portion contiguous thereto such that the lesion portion and the previously formed lesion portion together form a lesion of increased width. For example, the member 18 can be moved laterally or transversely of first lesion portion 538a and positioned contiguous thereto in side by side relation to form a fourth lesion portion merging with the first lesion portion 538a. Thereafter, the member 18 can be manually moved longitudinally, as described for formation of the second and third lesion portions, to form fifth and sixth lesion portions contiguous and in side by side relation with second and third lesion portions 538b and 538c, respectively. In this manner, a single discrete lesion of desired final size and configuration can be created in the tissue from a plurality of lesion portions formed with a single ultrasound emitting member, and the final size lesions can have any desired length and width.

The ultrasound ablation devices 112 and 212 can be used to form any of the lesions described above by selecting and programming the transducer elements 128 and 228 for the range of motion needed to obtain the desired lesion size and shape. In particular, the range of longitudinal movement selected for the transducer elements determines the length of the lesions, while the range of transverse movement selected for the transducer elements determines the width of the lesions. As the transducer elements scan the tissue with focused ultrasound energy, the focusing zones are moved within the tissue but remain at the predetermined depth within the tissue.

The ultrasound ablation device 312 can be used to form any of the lesions described above by selecting and programming the ultrasound emitting member 318 for the range of extension and/or retraction needed to obtain the desired lesion size and shape and, if necessary, manually moving the member 318 laterally along the tissue surface. The range of longitudinal extension and retraction of the member 318 determines the length of the lesion. The width of the lesion is determined by the intensity of the ultrasound energy and the duration of ultrasound energy delivery to the tissue. A larger lesion width can be obtained by manually moving the member 318 laterally or transversely, as described above for member 18, from location to location in a desired number of increments and scanning the tissue with ultrasound via extension and retraction of the member 318 to obtain a plurality of contiguous lesion portions together forming a lesion of desired final width. Extension and retraction of the member 318 is accomplished automatically and is representative of mechanical scanning. The active face can be maintained in contact with the tissue as the member 318 is reciprocated, and the membrane can be made of a slippery material to facilitate reciprocation and reduce friction between the active face and the tissue surface. Of course, an ultrasound transmitting gel can be disposed between the active faces of any of the ultrasound emitting members and the tissue surface. As the member 318 is moved along the tissue, the focusing zone is also moved but remains the predetermined depth beneath the tissue surface.

The methods of the present invention allow tongue reduction to be performed with minimal trauma and pain for the patient and with faster healing and recovery times. The mucosa or other external surface or layer of tissue is preserved so that no external wound is presented or exposed. A single ablation treatment in accordance with the present invention may be sufficient to eliminate various airway related disorders or conditions since a lesion of sufficient size may be obtained with a single treatment. By controlling the delivery of ultrasound energy to the tissue, the temperature to which the tissue is heated by the ultrasound energy can be controlled to avoid undesired patient responses. The ultrasound emitting members can be provided with sensors for monitoring the amount of ultrasound energy delivered to the tissue and/or for detecting the temperature to which the tissue is heated, which can be provided as feedback to the controller. The delivery of ultrasound energy to the tissue can be controlled to achieve a selected temperature in the tissue, a selected amount of ablation or a desired duration of ultrasonic energy delivery. The ultrasound emitting members can be designed to be reusable and thusly can be capable of being sterilized to medical standards. The ultrasound emitting members can be introduced at internal operative sites through catheters or sleeves with the ultrasound emitting members disposed within the catheters or sleeves during introduction and being extended from the catheters or sleeves following introduction at the operative sites. The ultrasound emitting members can be immobilized during use as may be accomplished with various types of stabilizing members provided on the shafts or on the ultrasound emitting members. Any number of lesions can be formed in the tongue with each lesion surrounded by normal, undamaged tissue or with the lesions contiguous to, in abutment with or overlapping one another to form a single lesion. The ultrasound emitting members, the transducers and/or the transducer elements can be moved relative to the tissue to scan target areas with focused ultrasound energy, and such scanning can be accomplished in various diverse ways including manually and automatically. Automatic scanning can be accomplished mechanically and/or electrically.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of thermal ablation of the tongue comprising the steps of introducing an ultrasound emitting member in a patient's oral cavity;

positioning the ultrasound emitting member adjacent an external surface of the tongue;

emitting ultrasound energy from the ultrasound emitting member into the tissue of the tongue;

focusing the ultrasound energy at a focusing zone within the tissue of the tongue such that the ultrasound energy converges at the focusing zone, the focusing zone being contained in a target area disposed below and not including the external surface;

heating the tissue at the target area with the focused ultrasound energy to create an ablative lesion confined to the target area; and withdrawing the ultrasound emitting member from the oral cavity.

2. The method of thermal ablation of the tongue recited in claim 1 wherein said step of positioning includes positioning the ultrasound emitting member in contact with the external surface at the base of the tongue.

3. The method of thermal ablation of the tongue recited in claim 2 wherein said step of positioning includes positioning the ultrasound emitting member on the external surface at a location aligned with the target area.

4. The method of thermal ablation of the tongue recited in claim 3 wherein said step of emitting includes activating a transducer of the ultrasound emitting member to emit the ultrasound energy.

5. A method of thermal ablation of the tongue comprising the steps of
   introducing an ultrasound emitting member in a patient's oral cavity;
   positioning the ultrasound emitting member adjacent an external surface of the tongue, said step of positioning including positioning the ultrasound emitting member in contact with the external surface at the base of the tongue and at a location aligned with a target area within the tongue, the target area being disposed below the external surface, said step of positioning including acoustically coupling a transducer of the ultrasound emitting member with the tissue via an acoustic coupling medium;
   emitting ultrasound energy from the ultrasound emitting member into the tissue of the tongue, said step of emitting including activating the transducer of the ultrasound emitting member to emit the ultrasound energy;
   focusing the ultrasound energy within the tissue of the tongue below the external surface;
   heating the tissue at the target area within the tongue with the focused ultrasound energy to create an ablative lesion at the target area; and
   withdrawing the ultrasound emitting member from the oral cavity.

6. The method of thermal ablation of the tongue recited in claim 5 wherein said step of coupling includes coupling the transducer with the tissue via an acoustic fluid disposed between the tissue and the transducer.

7. The method of thermal ablation of the tongue recited in claim 4 wherein said step of focusing includes focusing the ultrasound energy with a lens of the ultrasound emitting member.

8. The method of thermal ablation of the tongue recited in claim 7 wherein said step of focusing includes focusing the ultrasound energy due to a curvature of the lens.

9. The method of thermal ablation of the tongue recited in claim 4 wherein said step of activating includes supplying electrical energy to a piezoelectric element of the transducer and vibrating the piezoelectric element in response to the electrical energy.

10. A method of thermal ablation of the tongue comprising the steps of
    introducing an ultrasound emitting member in a patient's oral cavity;
    positioning the ultrasound emitting member adjacent an external surface of the tongue, said step of positioning including positioning the ultrasound emitting member in contact with the external surface at the base of the tongue and at a location aligned with a target area within the tongue, the target area being disposed below the external surface, said step of positioning including acoustically coupling a piezoelectric element of a transducer of the ultrasound emitting member with the tissue via an acoustic coupling medium disposed between the tissue and the piezoelectric element;
    emitting ultrasound energy from the ultrasound emitting member into the tissue of the tongue, said step of emitting including activating the transducer of the ultrasound emitting member to emit the ultrasound energy, said step of activating including supplying electrical energy to the piezoelectric element of the transducer and vibrating the piezoelectric element in response to the electrical energy;
    focusing the ultrasound energy within the tissue of the tongue below the external surface;
    heating the tissue at the target area within the tongue with the focused ultrasound energy to create an ablative lesion at the target area; and
    withdrawing the ultrasound emitting member from the oral cavity.

11. A method of thermal ablation of the tongue comprising the steps of
    introducing an ultrasound emitting member in a patient's oral cavity;
    positioning the ultrasound emitting member adjacent an external surface of the tongue, said step of positioning including positioning the ultrasound emitting member in contact with the external surface at the base of the tongue and at a location aligned with a target area within the tongue, the target area being disposed below the external surface;
    emitting ultrasound energy from the ultrasound emitting member into the tissue of the tongue, said step of emitting including activating a transducer of the ultrasound emitting member to emit the ultrasound energy, said step of activating including supplying electrical energy to a piezoelectric element of the transducer and vibrating the piezoelectric element in response to the electrical energy;
    focusing the ultrasound energy within the tissue of the tongue below the external surface, said step of focusing including focusing the ultrasound energy due to a curvature of the piezoelectric element;
    heating the tissue at the target area within the tongue with the focused ultrasound energy to create an ablative lesion at the target area; and
    withdrawing the ultrasound emitting member from the oral cavity.

12. The method of thermal ablation of the tongue recited in claim 1 and further including the step of sensing the temperature of the tissue.

13. The method of thermal ablation of the tongue recited in claim 12 wherein said step of sensing includes sensing the temperature of the tissue near the external surface.

14. The method of thermal ablation of the tongue recited in claim 12 and further including the step of terminating the emission of ultrasound energy into the tissue in response to sensing of a predetermined temperature.

15. The method of thermal ablation of the tongue recited in claim 4 and further including the step of cooling the transducer.

16. The method of thermal ablation of the tongue recited in claim 1 and further including the step of cooling the tissue of the tongue adjacent the external surface.

17. The method of thermal ablation of the tongue recited in claim 16 wherein said step of cooling includes supplying cooling fluid to the ultrasound emitting member.

18. The method of thermal ablation of the tongue recited in claim 1 wherein said step of heating includes heating the tissue at the target area to a temperature in the range of 60 to 100° Celsius.

19. A method of tongue reduction comprising the steps of
    introducing an ultrasound emitting member in a patient's oral cavity;
    positioning an active face of the ultrasound emitting member against an external surface of the tongue;

emitting ultrasound energy from the ultrasound emitting member into the tissue of the tongue;

focusing the ultrasound energy within the tongue at a focusing zone disposed a predetermined distance beneath the external surface;

heating the tissue at a target area within the tongue, disposed beneath the external surface, with the focused ultrasound energy to create an internal lesion at the target area; and withdrawing the ultrasound emitting member from the oral cavity.

20. The method of tongue reduction recited in claim 19 wherein said step of positioning includes positioning the ultrasound emitting member on the base of the tongue.

21. The method of tongue reduction recited in claim 20 wherein said step of focusing includes focusing the ultrasound energy so that the focusing zone is located the predetermined distance from the active face in a direction perpendicular to the active face.

22. The method of tongue reduction recited in claim 21 wherein said step of focusing includes focusing the ultrasound energy so that the focusing zone is located the predetermined distance from the external surface of the tongue in a direction perpendicular to the external surface.

23. The method of tongue reduction recited in claim 19 wherein said step of heating includes heating the tissue so that the target area begins at a beginning margin located approximately 4 mm beneath the external surface.

24. The method of tongue reduction recited in claim 23 wherein said step of heating includes heating the tissue so that the target area ends at an ending margin located 10 to 20 mm beneath the external surface and has a depth of 6 to 16 mm between the beginning and ending margins.

25. The method of tongue reduction recited in claim 19 wherein said step of heating includes heating the tissue for a duration in the range of 2 to 45 seconds.

26. The method of tongue reduction recited in claim 19 and further including the step of allowing part of the lesion to remain as unabsorbed scar tissue in the tongue whereby vibration of the tongue is inhibited.

27. The method of tongue reduction recited in claim 19 and further including the step of allowing the lesion to be at least partly absorbed by the patient's body such that the tongue is reduced in size.

28. A method of thermal ablation of the tongue to treat airway associated disorders, including airway obstructions, snoring disorders and sleep apnea syndrome, comprising the steps of introducing an ultrasound emitting member in a patient's oral cavity;

positioning the ultrasound emitting member at a location on the mucosa of the tongue;

emitting ultrasound energy from the ultrasound emitting member into the tissue of the tongue;

focusing the ultrasound energy within the tongue at at least one focusing zone contained in a target area disposed below the mucosa such that the ultrasound energy is of higher intensity in tissue at the at least one focusing zone than in tissue surrounding the target area;

heating the tissue with the focused ultrasound energy such that the target area is heated to an ablative temperature to form a lesion at the target area while tissue surrounding the target area is not heated to a damaging level; and withdrawing the ultrasound emitting member from the oral cavity.

29. The method of thermal ablation of the tongue recited in claim 28 wherein said step of heating includes heating the tissue so that the lesion has a beginning margin located approximately 4 mm below the external surface.

30. The method of thermal ablation of the tongue recited in claim 29 wherein said step of heating includes heating the tissue so that the lesion has a depth of 6 to 16 mm.

31. The method of thermal ablation of the tongue recited in claim 30 wherein said step of heating includes heating the tissue so that the lesion has a length of 10 to 36 mm.

32. The method of thermal ablation of the tongue recited in claim 31 wherein said step of heating includes heating the tissue so that the lesion has a width of 10 to 25 mm.

33. The method of thermal ablation of the tongue recited in claim 32 wherein said step of heating includes heating the tissue to form a generally circular lesion having a diameter of approximately 10 mm.

34. The method of thermal ablation of the tongue recited in claim 32 wherein said step of heating includes heating the tissue to form a single, generally square lesion having a length of substantially 18 mm and a width of substantially 18 mm.

35. The method of thermal ablation of the tongue recited in claim 32 wherein said step of heating includes heating the tissue to form a generally rectangular lesion having a length of substantially 36 mm and a width of substantially 25 mm.

36. The method of thermal ablation of the tongue recited in claim 32 wherein said step of heating includes heating the tissue to form a single lesion at a location centrally located between the sides of the tongue.

37. The method of thermal ablation of the tongue recited in claim 28 wherein said step of focusing includes focusing the ultrasound energy at at least one first focusing zone contained in a first target area and said step of heating includes heating the tissue to form a first lesion at the first target area, said step of focusing further includes focusing the ultrasound energy within the tongue at at least one second focusing zone contained in a second target area disposed below the mucosa such that the ultrasound energy is of higher intensity in tissue at the at least one second focusing zone than in tissue surrounding the second target area and said step of heating further includes heating the tissue with the ultrasound energy focused at the at least one second focusing zone such that the second target area is heated to an ablative temperature to form a second lesion at the second target area while tissue surrounding the second target area is not heated to a damaging level.

38. The method of thermal ablation of the tongue recited in claim 28 wherein said step of heating includes heating the tissue to form a first lesion at a first target area and further including, subsequent to said step of heating, the steps of positioning the ultrasound emitting member at another location on the mucosa, emitting ultrasound energy from the ultrasound emitting member into the tissue of the tongue, focusing the ultrasound energy within the tongue at at least one second focusing zone contained in a second target area disposed below the mucosa such that the ultrasound energy is of higher intensity in tissue at the at least one second focusing zone than in tissue surrounding the second target area and heating the tissue with the ultrasound energy focused at the at least one second focusing zone such that the second target area is heated to an ablative temperature to form a second lesion at the second target area.

39. The method of thermal ablation of the tongue recited in claim 38 wherein said step of heating the tissue to form the first lesion includes heating the tissue to form a first lesion portion at the first target area and said step of heating the tissue to form the second lesion includes heating the tissue to form a second lesion portion at the second target area contiguous with the first lesion portion so that the first and second lesion portions together form a single lesion of larger size.

* * * * *

UNITED STATES PATENT AND TRADEMARK OFFICE
CERTIFICATE OF CORRECTION

PATENT NO.        : 6,413,254 B1
APPLICATION NO.   : 09/487707
DATED             : July 2, 2002
INVENTOR(S)       : James B. Hissong et al.

It is certified that error appears in the above-identified patent and that said Letters Patent is hereby corrected as shown below:

On the title page (item 54) + Column 1, Line 1

In the title the word, "Method" should read --Methods--.

Column 26, line 31, that portion of the claim reading "tar get" should read --target--.

Signed and Sealed this

Twenty-ninth Day of August, 2006

JON W. DUDAS
*Director of the United States Patent and Trademark Office*